United States Patent
Liu et al.

(10) Patent No.: US 8,529,920 B2
(45) Date of Patent: Sep. 10, 2013

(54) LOW PH RETINOID TOPICAL COMPOSITIONS

(75) Inventors: Limin Liu, Palatine, IL (US); Ralph Spindler, Palatine, IL (US); Gholam-Reza Vakili-Tahami, Naperville, IL (US)

(73) Assignee: Amcol International Corporation, Hoffman Estates, IL (US)

( * ) Notice: Subject to any disclaimer, the term of this patent is extended or adjusted under 35 U.S.C. 154(b) by 23 days.

(21) Appl. No.: 13/062,021

(22) PCT Filed: Sep. 9, 2009

(86) PCT No.: PCT/US2009/056319
§ 371 (c)(1),
(2), (4) Date: Apr. 14, 2011

(87) PCT Pub. No.: WO2010/030636
PCT Pub. Date: Mar. 18, 2010

(65) Prior Publication Data
US 2011/0189249 A1     Aug. 4, 2011

Related U.S. Application Data

(60) Provisional application No. 61/096,506, filed on Sep. 12, 2008.

(51) Int. Cl.
*A61K 9/16*     (2006.01)
*A61K 9/107*    (2006.01)
*A61K 8/02*     (2006.01)

(52) U.S. Cl.
USPC ........... 424/401; 424/489; 514/725; 514/164; 514/557

(58) Field of Classification Search
None
See application file for complete search history.

(56) References Cited

U.S. PATENT DOCUMENTS

| | | | |
|---|---|---|---|
| 4,948,818 A | 8/1990 | Carmody et al. | |
| 4,962,133 A | 10/1990 | Chromecek et al. | |
| 4,962,170 A | 10/1990 | Chromecek et al. | |
| 5,137,178 A | 8/1992 | Stokes et al. | |
| 5,677,407 A | 10/1997 | Sojka | |
| 5,712,358 A | 1/1998 | Sojka | |
| 5,777,054 A | 7/1998 | Sojka | |
| 5,830,960 A | 11/1998 | Sojka | |
| 5,830,967 A | 11/1998 | Sojka | |
| 5,834,577 A | 11/1998 | Sojka | |
| 5,837,790 A | 11/1998 | Sojka | |
| 5,851,538 A | 12/1998 | Froix et al. | |
| 5,914,116 A | 6/1999 | Suares et al. | |
| 5,935,589 A | 8/1999 | Mukherjee et al. | |
| 5,955,552 A | 9/1999 | Sojka | |
| 6,107,429 A | 8/2000 | Sojka | |
| 6,248,849 B1 | 6/2001 | Sojka | |
| 6,387,995 B1 | 5/2002 | Sojka | |
| 6,468,549 B1 * | 10/2002 | Dupuis et al. ............ 424/401 |
| 6,491,953 B1 | 12/2002 | Sojka et al. | |
| 6,544,531 B1 | 4/2003 | Cole et al. | |
| 7,396,526 B1 | 7/2008 | Cole et al. | |
| 2007/0178058 A1 * | 8/2007 | Ramirez et al. ........... 424/70.28 |
| 2008/0069779 A1 | 3/2008 | Tamarkin et al. | |
| 2008/0139518 A1 | 6/2008 | Purcell | |

FOREIGN PATENT DOCUMENTS

| EP | 0440398 A1 | 8/1991 |
| EP | 0832643 A2 | 4/1998 |
| WO | WO-9953904 A2 | 10/1999 |
| WO | WO-01/85129 A2 | 11/2001 |
| WO | WO-2005/107710 A2 | 11/2005 |

OTHER PUBLICATIONS

International Search Report for corresponding International application No. PCT/US2009/056319, dated Dec. 30, 2009.

* cited by examiner

*Primary Examiner* — Rachael E Bredefeld
(74) *Attorney, Agent, or Firm* — Marshall, Gerstein & Borun LLP

(57) ABSTRACT

A low pH composition containing a retinol and a method for treating skin is disclosed. The composition contains (a) a retinoid and (b) an active acid, like an alpha-hydroxy acid or a beta-hydroxy acid, and has a pH of less than 5.

21 Claims, No Drawings

LOW PH RETINOID TOPICAL COMPOSITIONS

CROSS-REFERENCE TO RELATED APPLICATIONS

This is the U.S. National Phase application PCT/US2009/056319, filed Sep. 9, 2009, which claims the benefit of U.S. provisional application No. 61/096,506, filed Sep. 12, 2008, incorporated herein by reference in its entirety.

BACKGROUND OF THE INVENTION

Retinol and its derivatives display key regulatory functions in epidermal growth and differentiation. Topically-applied retinol reduces fine lines and wrinkles by skin absorption, which leads to increases in the rate of collagen production. However, retinol is sensitive to oxidation and photolysis, and rapidly converts to the cis-isomer and degrades when exposed to light or oxygen. The degradation of retinol can be accelerated by acidic compounds, such as alpha and beta-hydroxy acids, at pH values below 5.0.

Alpha-hydroxy acids are a class of carboxylic acid compounds substituted with a hydroxy group on the carbon atom adjacent to the carboxyl group. Alpha-hydroxy acids also are used for skin rejuvenation in topical skin care products. Alpha-hydroxy acids exfoliate dead cells from the epidermis to give a more youthful appearance. Alpha-hydroxy acids work best at low pH values of 3.0 to 4.0.

Salicylic acid is a key ingredient in many skin-care products for the treatment of acne, psoriasis, calluses, corns, keratosis pilaris, and warts. It is the sole beta hydroxy acid widely used in cosmetics. Salicylic acid is a metabolite of aspirin being the product of esterase hydrolysis in the liver. It has some anti-inflammatory properties, and is less irritating to skin and can work at much lower concentrations than alpha-hydroxy acids. Unlike alpha-hydroxy acids, salicylic acid is lipid soluble. It can penetrate deeper into epidermis and unclogs the pores or the openings of sebaceous glands by removing dead skin cells that prevent the sebum from exiting. This accelerates the production of fresh skin cells. Salicylic acid also works best at a low pH value of 3.0 to 4.0.

It is challenging to combine a retinoid, which is incompatible with acids at low pH, with an alpha-hydroxy acid or salicylic acid, which are more effective at low pH, to achieve addition or synergistic benefits. Formulating a retinoid is a challenge in general due to its well known oxidative and photo-induced instabilities. These challenges can be met, especially through the use of the proper choice of antioxidants and/or packaging the product in a container that effectively protects the retinoid.

Additionally, the use of a microparticle delivery system can improve the stability of retinoids. In addition to the well known sensitivities of retinoids in terms of oxidation and photo-induced isomerization, acidic conditions promote the dimerization of retinoids, which cannot be prevented by any of the strategies discussed above for the stabilization of retinoids.

Combinations of retinol and an alpha-hydroxy carboxylic acid have been reported in U.S. Pat. No. 5,935,589. The active agents are present in two separate emulsions within a single package. Retinol is present in an oil-in-water emulsion at a neutral pH. An alpha-hydroxy carboxylic acid is positioned within a water-in-oil emulsion. The two emulsions then are carefully formulated in a single package for use. One problem is that the active agents need to be more concentrated, which may induce higher irritation on skin. Another problem is that the two emulsions are in direct contact with each other and can mix together during storage resulting in fast retinol degradation, i.e., only 40% of the original retinol is retained after storage at 41° C. for 24 weeks.

One solution to overcome the incompatibility between retinoids and dermatologically active acids is to package the two active agents in separate containers for storage. U.S. Patent Publication No. 2008/0139518 discloses a kit for treatment of skin conditions comprising a retinoid and salicylic acid characterized by synergistic activity. In such a kit, the active agents can be stabilized in different containers. The intended dosage can be administrated in combination, in succession, or in some other close proximity of time. U.S. Pat. No. 5,914,116 discloses releasably lockable stacked jars and dual compartment pumps to store the incompatible active agents separately. These packages are designed to deliver the active agents non-simultaneously. U.S. Pat. No. 5,137,178 discloses a squeezable dual tube dispenser which allows for simultaneous delivery of separate compositions held in separate compartments. One problem with the dual-chambers is that the active agents must be doubly concentrated. High concentrations result in greater irritation to skin, and also may adversely affect formulation stability. In addition, the cost of dual chamber packaging, and the resultant cost to consumers, can be prohibitive for massive market applications. Therefore, a less costly system of achieving the same stability is highly desired.

U.S. Pat. Nos. 6,544,531 and 7,396,526 disclose skin care compositions that contain both retinol and an acid in a single formulation. A volatile base, such as ammonium hydroxide, is used to adjust formulation pH to 5.0 or above to provide good storage stability. After application on the skin, the pH of the formulation drops below 5.0 due to evaporation of ammonia during drying to activate the acids and provide skin benefits. NEUTROGENA Clear Skin anti-wrinkle cream is one commercial product that utilizes a volatile base to combine retinol and salicylic acid in a single composition. The composition contains 2% salicylic acid and 0.071% retinol, and has a pH of 6.3. A study showed that the cream product retains 49% of the original amount of retinol after 24 weeks storage at 40° C. Another disadvantage of this type of composition is that ammonia has a characteristic odor, and may irritate skin, eyes, and respiratory systems.)

For all the above reasons, a strong need exists to develop a stable composition that combines retinol and/or other retinoids with acids in a single package. In accordance with the present invention, a topical composition comprising these active ingredients in a single formulation is provided, wherein the retinoid is stabilized to a much higher degree than in current formulations.

SUMMARY OF THE INVENTION

The present invention provides a composition for topical application that comprises (a) a retinoid and (b) a beta-hydroxy acid or an alpha-hydroxy carboxylic acid in a single package, wherein the composition has a pH below 5.0. For an example, a composition containing 0.5% salicylic acid by weight and 0.1% retinol by weight, and having a pH of 4.5, that retains 86% retinol after 24 weeks storage at 40° C. in a simulated 2 year shelf-life at ambient temperature.

In one aspect of the invention, the topical composition is a water-in-oil emulsion. The composition retains at least 70% retinol after 24 weeks storage at 40° C. In one embodiment, the acid is present in the aqueous phase and the retinoid is present in the oil phase. In another embodiment, the retinoid is loaded onto polymeric microparticles and is distributed between the polymer microparticles and the oil phase. While not being bound by theory, the strong oil-water interface at least partially attributed to the combined use of an emulsifier and a thickener, and the employment of a stabilizing system, play important roles in stabilizing the retinoid in the composition.

In another aspect, the present invention provides a stable retinoid composition having a pH less than 5.0.

Incorporating a beta-hydroxy or an alpha-hydroxy acid into water-in-oil emulsions typically results in instability and phase separation during storage. Therefore, in another aspect, the present invention provides a stable water-in-oil composition that contains a dermatologically active acid.

In still another aspect, the present invention provides a water-in-oil composition utilizing a chelating agent in the aqueous phase and an oil-soluble antioxidant in the oil phase to stabilize the retinoid in the composition.

Another aspect of the invention is the use of a microparticle delivery system on which the retinoid is loaded, or entrapped, together with suitable stabilizing ingredients. The retinoid-containing microparticles help improve the stability of the retinoid, and also help reduce irritation after the composition is applied to the skin. In accordance with the present invention, effective retinoid stabilization is achieved by a polymeric microparticle loaded with a retinoid.

Another aspect of the present method is to provide a method of treating skin of a mammal, including humans, comprising applying a water-in-oil emulsion composition comprising (a) a retinoid and (b) salicyclic acid and/or an alpha-hydroxy carboxylic acid to a skin surface of the mammal. The retinoid can be (a) incorporated directly into the emulsion and/or (b) loaded onto polymeric microparticles that are incorporated into the emulsion. The method improves the appearance and condition of the skin.

Yet another aspect of the present invention is to provide an emulsified composition containing (a) a retinoid, free and/or loaded onto polymeric microparticles and (b) salicyclic acid and/or an alpha-hydroxy carboxylic acid, and use of the composition as a topical skin care product.

These and other novel aspects of the present invention will become apparent from the following detailed description of the preferred embodiments.

DETAILED DESCRIPTION OF THE INVENTION

The present invention is directed to a composition comprising (a) a retinoid and (b) a beta-hydroxy acid and/or an alpha-hydroxy acid, and a pH of about 3.0 to 5.0, preferably about 3.5 to about 4.5, wherein the retinoid exhibits unexpected storage stability. The retinoid can be present as the free compound and/or entrapped in polymeric microparticles. The pH of the composition can be adjusted by volatile or nonvolatile bases, such as sodium hydroxide or triethanolamine.

The present compositions are in the form of a water-in-oil emulsion, and contain about 20 to about 50%, by weight, oil phase and about 50 to about 80%, by weight, water phase. The dermatologically active acid is present in the oil phase, and the retinoid is present in the oil phase, or is partitioned between the oil phase and, if present, the polymeric microparticle.

A retinoid in the composition can be include, both naturally occurring and synthetic compounds having the general structure of vitamin A (retinol) and variations of that structure having similar biological and pharmacological activity as retinol. Examples of retinoids include, but are not limited to, all-trans retinol, retinol, retinal, retinyl acetate, retinaldehyde, retinyl palmitate, retinoic acid, retinyl propionate, retinyl linoleate, dehydroretinol, eretinate, eretrin, motretinide, a synthetic retinoid, and mixtures thereof. U.S. Pat. No. 5,851,538, incorporated herein by reference, discloses several additional useful retinoids.

The amount of retinoid in the composition is about 0.03 to about 10%, preferably about 0.05 to about 5%, and more preferably about 0.1 to about 2%, by total weight of the composition. The retinoid can be dispersed in an oil phase, can be entrapped into adsorbent polymer microparticles, or both.

Absorbent polymeric microparticles useful in the present invention have an ability to absorb several times their weight of a liquid compound, such as a retinoid. One preferred class of adsorbent microparticles is prepared by a suspension polymerization technique, as set forth in U.S. Pat. Nos. 5,677,407; 5,712,358; 5,777,054; 5,830,967; 5,834,577, 5,955,552; and 6,107,429, each incorporated herein by reference (available commercially under the tradename of POLY-PORE® E200, INCI name, allyl methacrylate copolymer, from AMCOL International, Hoffman Estates, Ill.). Another preferred class of adsorbent microparticles is prepared by a precipitation polymerization technique, as set forth in U.S. Pat. Nos. 5,830,960; 5,837,790, 6,248,849; and 6,387,995, each incorporated herein by reference (sold under the tradename of POLY-PORE® L200 by AMCOL International, Hoffman Estates, Ill.). These adsorbent microparticles also can be modified after the incorporation of an active compound to modify the rate of release of such a compound, as set forth in U.S. Pat. No. 6,491,953, incorporated herein by reference.

Another useful class of adsorbent polymers prepared by a precipitation polymerization technique is disclosed in U.S. Pat. Nos. 4,962,170; 4,948,818; and 4,962,133, each incorporated herein by reference, and are commercially available under the tradename POLYTRAP® from AMCOL International. Other useful, commercially available adsorbent polymers include, for example, MICROSPONGE® (a copolymer of methyl methacrylate and ethylene glycol dimethacrylate), available from AMCOL International and Poly-HIPE polymers (e.g., a copolymer of 2-ethylhexyl acrylate, styrene, and divinylbenzene) available from Biopore Corporation, Mountain View, Calif.

In particular, the adsorbent polymer microparticles prepared by the suspension polymerization technique, e.g., POLY-PORE® E200, are a highly porous and highly crosslinked polymer in the form of open (i.e., broken) spheres and sphere sections characterized by a mean unit particle size of about 0.5 to about 3,000 microns, preferably about 0.5 to about 300 microns, more preferably about 0.5 to about 100 microns, and most preferably about 0.5 to about 80 microns. A significant portion of the spheres is about 20 microns in diameter.

The polymeric microparticles are oil and water adsorbent, and have an extremely low bulk density of about 0.008 gm/cc to about 0.1 gm/cc, preferably about 0.009 gm/cc to about 0.07 gm/cc, and more preferably about 0.0095 gm/cc to about 0.04-0.05 gm/cc. The microparticles are capable of holding and releasing oleophilic (i.e., oil soluble or dispersible), as well as hydrophilic (i.e., water soluble or dispersible), active agents, individually, or both oleophilic and hydrophilic compounds simultaneously.

The adsorbent polymer microparticles prepared by the suspension polymerization technique include at least two polyunsaturated monomers, preferably allyl methacrylate and an ethylene glycol dimethacrylate, and, optionally, monounsaturated monomers. The microparticles are characterized by being open to their interior, due either to particle fracture upon removal of a porogen after polymerization or to subsequent milling. The microparticles have a mean unit diameter of less than about 50 microns, preferably less than about 25 microns, and have a total adsorption capacity for organic liquids, e.g., mineral oil, that is at least about 72% by weight, preferably at least about 93% by weight, and an adsorption capacity for hydrophilic compounds and aqueous solutions of about 70% to about 89% by weight, preferably about 75% to about 89% by weight, calculated as weight of material adsorbed divided by total weight of material adsorbed plus dry weight of polymer. In a preferred embodiment, the broken sphere microparticles are characterized by a mean unit diameter of about 1 to about 50 microns, more preferably of about 1 to about 25 microns, most preferably, of about 1 to about 20 microns.

Preferred polymeric microparticle delivery systems comprise a copolymer of allyl methacrylate and ethylene glycol dimethacrylate, a copolymer of ethylene glycol dimethacrylate and lauryl methacrylate, a copolymer of methyl methacrylate and ethylene glycol dimethacrylate, a copolymer of 2-ethylhexyl acrylate, styrene, and divinylbenzene, and mixtures thereof. Specific polymeric microparticles useful in the present invention can be the previously described POLY-PORE® E200, POLY-PORE® L200, POLYTRAP® 6603, POLYTRAP® 7603, MICROSPONGE® entrapments, or Poly-HIPE particles, for example.

To function as a delivery system for a retinoid, the retinoid is incorporated onto the polymeric microparticles. This can be accomplished by spraying or adding the retinoid either directly to the microparticles in such a manner that an essentially homogeneous distribution of the retinoid is achieved on all the microparticles. Alternatively, if the retinoid is a solid compound, the retinoid first is dissolved in a suitable volatile solvent, the resulting solution is added to the microparticles, then the volatile solvent is removed under vacuum with optional gentle heating. In some cases, this process is repeated several times to achieve a desired loading level of the retinoid. Another method of loading a solid retinoid that is not readily soluble in a volatile solvent is to first disperse the solid in a suitable carrier, such as polyether or polyol, and then add the dispersion directly to the polymeric microparticles.

The load of the retinoid in and on the polymeric microparticles can be about 1 to about 80 wt. %, when the retinoid is a solid material at room temperature (i.e., about 23° C. to 25° C.), or in a preferred amount of about 5 to about 67 wt. %, or in the more preferred amount of about 10 to about 50 wt. %, by total weight of the loaded microparticles.

In some cases, it is possible to further protect the tinoid by adding a second material, usually a liquid or waxy material, to the loaded microparticles after the retinoid has been entrapped. After entrapping the retinoid, a barrier layer (i.e., a secondary entrapment), optionally, can be applied to the loaded microparticles to prevent rapid diffusion of the retinoid from the microparticle. Also, the melting point of the barrier layer can be selected such that it melts at a temperature higher than the highest temperature that the microparticles will be exposed either during storage in the final formulated product or during accelerated aging of the final formulation.

Examples of materials that can be used as a barrier layer or a secondary entrapment, ude, but are not limited to, low melting alcohols ($C_8$ through $C_{20}$) and fatty alcohols ethoxylated with one to three moles of ethylene oxide. Examples of fatty alcohols and alkoxylated fatty alcohols include, but are not limited to, behenyl alcohol, caprylic alcohol, cetyl alcohol, cetaryl alcohol, decyl alcohol, lauryl alcohol, isocetyl alcohol, myristyl alcohol, oleyl alcohol, stearyl alcohol, tallow alcohol, stearety-2, ceteth-1, cetearth-3, and laureth-2. Additional fatty alcohols and alkoxylated alcohols are listed in the *International Cosmetic Ingredient Dictionary and Handbook*, Tenth Edition, Volume 3, pages 2127 and pages 2067-2073 (2006), incorporated herein by reference.

Another class of materials that can be used as a barrier layer is the $C_8$ to $C_{12}$ fatty acids, including, but not limited to, stearic acid, capric acid, behenic acid, caprylic acid, lauric acid, myristic acid, tallow acid, oleic acid, palmitic acid, isostearic acid and additional fatty acids listed in the *International Cosmetic Ingredient Dictionary and Handbook*, Tenth Edition, Volume 3, page 2126-2127, incorporated herein by reference. The barrier material also can be a hydrocarbon, like mineral oil, 1-decene dimer, polydecene, paraffin, petrolatum, vegetable-derived petrolatum or isoparafin.

Another class of barrier materials is waxes, like mink wax, carnauba wax, and candelilla wax, for example, and synthetic waxes, like silicone waxes, polyethylene, and polypropylene. Fats and oils can be useful barrier material agents, which include, for example, but are not limited to, lanolin oil, linseed oil, coconut oil, olive oil, menhaden oil, castor oil, soybean oil, tall oil, rapeseed oil, palm oil, and neatsfoot oil, and additional fats and oils listed in the *International Cosmetic Ingredient Dictionary and Handbook*, Tenth Edition, Volume 3, pages 2124-2126. Another useful class of barrier materials includes water-insoluble esters having at least 10 carbon atoms, and preferable 10 to about 32 carbon atoms. Numerous esters are listed in *International Cosmetic Ingredient Dictionary and Handbook*, Tenth Edition, Volume 3, pages 2115-2123.

Alternatively, a retinoid can be mixed with a molten waxy material, then entrapped in a microparticle delivery system. In the case of liquid retinoid, the waxy materials disclosed above as barrier materials also can be used as an additive for thickening the liquid retinoid and thereby help minimize premature diffusion of the retinoid from the microparticle.

The amount of the waxy material can be about 10% to about 67%, based on the weight of the loaded microparticles. In a more preferred embodiment, the amount of the waxy material is about 25% to about 50 wt. %, based on the total weight of the loaded microparticles.

A dermatologically active acid used in the present invention can be an alpha-hydroxy acid, a beta-hydroxy acid, ascorbic acid, derivatives thereof, or any mixture thereof. Examples of alpha-hydroxy acids include, but are not limited to, citric acid, glycolic acid, lactic acid, salts thereof, or mixtures thereof. The composition can contain 0.03% to about 10% alpha-hydroxy acid, preferably about 2 to about 10%, and more preferably about 4 to about 8%, by total weight of the composition. The beta-hydroxy acid comprises salicylic acid, salts thereof, or mixtures thereof. The composition can contain about 0.03 to about 10% salicylic acid, preferably about 0.1 to about 3%, and more preferably 0.5 to about 2%, by total weight of the composition. The dermatologically active acid is dissolved in an aqueous phase of the composition and the aqueous phase is adjusted to a pH below 5.0.

In one embodiment of the invention, the composition contains a chelating agent to stabilize the retinoid. The chelating agents form complexes with metal ions, especially with di- and trivalent ions, and therefore prevent these ions from interacting with the retinoids. The chelating agents can be any polycarboxyamino compound, such as ethylenediaminetetraacetic acid (EDTA), derivatives or salts thereof, and mixtures thereof. The amount of the chelating agent in the composition is about 0.01% to about 1%, and preferably from 0.02% to about 0.1%, by total weight of the composition. Other useful chelating agents include, but are not limited to, diethylenetriaminepentaacetic acid (DTPA), N-(hydroxy-ethyl)ethylenediaminetriacetate acid (HEDTA), nitrilotriacetic acid, salts thereof, and mixtures thereof.

A present composition also can incorporate an electrolyte, such as sodium chloride or potassium chloride, to stabilize the formulation at accelerated temperatures. The amount of electrolyte is 0%, or about 0.01% to about 5%, and more preferably about 0.5% to about 2%, by total weight of the composition.

An oil-soluble antioxidant used to stabilize the retinoid in the composition can be butylated hydroxytoluene (BHT), butylated hydroxyanisole (BHA), ascorbyl palmitate, alpha-tocopherot, or mixtures thereof in an amount of about 0.01% to about 1%, preferably from about 0.02% to about 0.1%, by total weight of the composition.

EXAMPLE 1

The following illustrates a representative composition of the present invention.

| Phase | Ingredients | % by Weight |
|---|---|---|
| A | Cetyl PEG/PPG-10/1 Dimethicone | 3.00 |
|   | Cyclopentasiloxane (and) Cyclohexasiloxane | 10.50 |
|   | Diisopropyl Adipate | 10.00 |
|   | Bis-PEG-12 Dimethicone Beeswax | 2.00 |
|   | BHT | 0.05 |
|   | Dimethicone | 1.30 |
| B | Sodium Chloride | 1.00 |
|   | Butylene Glycol | 5.00 |
|   | PEG-150 | 2.00 |
|   | Deionized Water | 61.90 |
|   | Disodium EDTA | 0.05 |
|   | Salicylic Acid | 0.50 |
|   | Sodium Hydroxide (50%) | 0.28 |
| C | Benzyl Alcohol | 1.00 |
|   | Phenoxyethanol | 0.90 |
| D | MICROSPONGE C116A (AMCOL)[1] | 0.52 |
|   | Total | 100.00 |

[1]MICROSPONGE C116A is methyl methacryliate/glycol dimethacrylate crosspolymer (and) retinol (and) tocopheryl acetate (and) ascorbic acid (and) disodium EDTA (and) propyl gallate (and) polysorbate 20 (and) BHT (retinol level - 23.5%), available from AMCOL Health and Beauty Solutions, Hoffman Estates, IL.

The composition was prepared using the following procedure, under yellow light.

1. Mix phase A ingredients and heat to 70-75° C.
2. Mix phase B ingredients and stir it until clear. Adjust pH to the target value of below 5.
3. Add phase C ingredients into phase B, the stir the resulting mixture until clear. Heat the mixture to 70-75° C.
4. Add the mixture of step 3. into phase A under agitation at 4000-5000 rpm. Then homogenize the resulting mixture at 7000-8000 rpm while the mixture cools to 30° C.
5. Change the homogenization to propeller-agitation. Keep agitating the mixture at 1000-2000 rpm.
6. When the mixture is below 25° C., add phase D under agitation. Keep agitating the mixture for 10 minutes.
7. Degas the composition and backfill with argon or nitrogen at least three times. Then pack the composition into amber glass jars for storage.

The composition was stable for a sustained period at accelerated temperatures. After storing in amber glass jars for 1 month at 50° C., no or little viscosity drop was observed. The lotion was packed into aluminum tubes for a retinol stability study.

A composition, containing 0.5% salicylic acid by weight and 0.1% retinol by weight, and having a pH of 4.5 was stored for 24 weeks at 40° C. (simulating 2 years shelf-life at ambient temperature). This study showed 86% of the 0.1% retinol was retained (20% overage was used). The composition retained 95% of the 0.1% retinol after storage at 45° C. for 12 weeks.

Another composition containing 2% glycolic acid by weight and 0.1% retinol by weight, and having a pH of 4.0, also was stored at 40° C. for 24 weeks. The composition retained 87% of the 0.1% retinol (10% overage was used). The composition retained 79% of the 0.1% retinol after storage at 45° C. for 12 weeks.

EXAMPLE 2

Another composition containing 0.5% salicylic acid by weight and 0.2% retinol by weight, and having a pH of 4.5, is prepared by the method set forth in Example 1.

| Phase | Ingredients | % by Weight |
|---|---|---|
| A | Cetyl PEG/PPG-10/1 Dimethicone | 2.88 |
|   | Cyclopentasiloxane (and) Cyclohexasiloxane | 9.90 |
|   | Diisopropyl Adipate | 9.40 |
|   | Bis-PEG-12 Dimethicone Beeswax | 1.25 |
|   | Hydrogenated Castor Oil | 0.50 |
|   | BHT | 0.10 |
|   | Dimethicone | 0.97 |
| B | Sodium Chloride | 0.50 |
|   | Butylene Glycol | 4.80 |
|   | PEG-150 | 1.90 |
|   | Deionized Water | 59.77 |
|   | Disodium EDTA | 0.10 |
|   | Salicylic Acid | 0.50 |
|   | Sodium Hydroxide (50%) | 0.28 |
| C | Benzyl Alcohol | 0.92 |
|   | Phenoxyethanol | 0.83 |
| D | Retinol 15D (BASF) | 1.35 |
|   | MICROSPONGE[2] | 4.05 |
|   | Total | 100.00 |

[2]MICROSPONGE is methyl methacrylate/glycol dimethacrylate crosspolymer, available from AMCOL Health and Beauty Solutions, Hoffman Estates, IL.

EXAMPLE 3

Another composition containing 2% salicylic acid by weight and 0.2% retinol by weight, and having a pH of 4.5, is prepared by the method set forth in Example 1.

| Phase | Ingredients | % by Weight |
|---|---|---|
| A | Cetyl PEG/PPG-10/1 Dimethicone | 2.88 |
|   | Cyclopentasiloxane (and) Cyclohexasiloxane | 9.90 |
|   | Diisopropyl Adipate | 9.40 |
|   | Bis-PEG-12 Dimethicone Beeswax | 1.25 |
|   | Hydrogenated Castor Oil | 0.50 |
|   | BHT | 0.05 |
|   | Dimethicone | 0.97 |
| B | Sodium Chloride | 0.50 |
|   | Butylene Glycol | 4.80 |
|   | PEG-150 | 1.90 |
|   | Deionized Water | 57.60 |
|   | Disodium EDTA | 0.10 |
|   | Salicylic Acid | 2.00 |
|   | Sodium Hydroxide (50%) | 1.00 |
| C | Benzyl Alcohol | 0.92 |
|   | Phenoxyethanol | 0.83 |
| D | Retinol 15D (BASF) | 1.35 |
|   | MICROSPONGE[2] | 4.05 |
|   | Total | 100.00 |

EXAMPLE 4

A composition containing 2% glycolic acid by weight and 0.1% retinol by weight, and having a pH of 4.0, also was stored at 40° C. for 24 weeks. The composition retained 87% of the 0.1% retinol (10% overage was used). The composition retained 79% of the 0.1% retinol after storage at 45° C. for 12 weeks. A representative composition prepared by the method of Example 1 is as follows:

| Phase | Ingredients | % by Weight |
|---|---|---|
| A | Cetyl PEG/PPG-10/1 Dimethicone | 3.00 |
|   | Cyclopentasiloxane (and) Cyclohexasiloxane | 11.00 |
|   | Diisopropyl Adipate | 10.00 |
|   | Bis-PEG-12 Dimethicone Beeswax | 1.00 |
|   | BHT | 0.05 |
|   | Dimethicone | 1.30 |
| B | Sodium Chloride | 0.50 |
|   | Deionized Water | 67.32 |
|   | Disodium EDTA | 0.05 |
|   | Glycolic Acid (70%) | 2.80 |
|   | Sodium Hydroxide (50%) | 1.43 |
| C | Benzyl Alcohol | 1.00 |
| D | MICROSPONGE C116A (AMCOL)[1] | 0.55 |
|   | Total | 100.00 |

EXAMPLE 5

Another composition, containing 2% glycolic acid by weight and 0.2% retinol by weight, and having a pH of 4.5, is prepared by the method set forth in Example 1.

| Phase | Ingredients | % by Weight |
|---|---|---|
| A | Cetyl PEG/PPG-10/1 Dimethicone | 3.00 |
|   | Cyclopentasiloxane (and) Cyclohexasiloxane | 11.00 |
|   | Diisopropyl Adipate | 10.00 |
|   | Bis-PEG-12 Dimethicone Beeswax | 1.25 |
|   | Hydrogenated Castor Oil | 0.50 |
|   | BHT | 0.05 |
|   | Dimethicone | 0.97 |
| B | Sodium Chloride | 0.50 |
|   | Butylene Glycol | 4.80 |
|   | Deionized Water | 58.83 |
|   | Disodium EDTA | 0.10 |
|   | Glycolic Acid (70%) | 2.85 |
|   | Sodium Hydroxide (50%) | 1.70 |
| C | Benzyl Alcohol | 0.92 |
|   | Phenoxyethanol | 0.83 |
| D | Retinol 15D (BASF) | 1.35 |
|   | MICROSPONGE[2] | 1.35 |
|   | Total | 100.00 |

EXAMPLE 6

A water-in-oil emulsion was prepared according to the procedure set forth in Example 1. The composition contained 0.5% glycolic acid and 0.1% retinol, and had a pH of 3.5. However, no chelating agent or antioxidant was included. Fast retinol degradation was observed, with the formulation retaining only 26% retinol by weight after storage at 45° C. for 4 weeks.

EXAMPLE 7 (COMPARATIVE)

For comparison, an oil-in-water emulsion comprising 0.1% retinol by weight and 0.35% glycolic acid by weight was prepared, as shown in the following table. After storage at 45° C. for 4 weeks, the composition only retained 24% retinol.

| Phase | Ingredient | % by Weight |
|---|---|---|
| A | Deionized Water | 69.74 |
|   | Magnesium Aluminum Silicate | 1.99 |
|   | Glycerin | 2.99 |
|   | Xanthan Gum | 0.08 |
|   | Glycolic Acid (70%) | 0.30 |
| B | Cetearyl Alcohol | 2.99 |
|   | Glyceryl Stearate & PEG 100 Stearate | 2.99 |
|   | Dimethicone, 100 cst | 1.99 |
|   | Myristyl Myristate | 0.50 |
|   | Cetearyl Acohol & Ceteareth-20 | 1.99 |
|   | Caprylic Capric Triglyceride | 8.96 |
|   | Dimethicone, 10 cst | 3.98 |
| C | Propylene Glycol (and) Diazolidinyl Urea (and) Methylparaben (and) Propylparaben | 1.00 |
| D | POLY-PORE 120RE (AMCOL)[2] | 0.50 |
|   | TOTAL | 100.00 |

[2]POLY-PORE 120RE is an allyl methacrylate crosspolymer (and) polysorbate 20 (and) retinol (and) BHT (retinol level - 20.5%), commonly available from AMCOL Health and Beauty Solutions, Hoffman Estates, IL.

A present composition is useful as personal care, cosmetic, and pharmaceutical compositions. The present compositions provide an effective delivery of a retinoid and an acid to the skin without irritation. The compositions also can be formulated with other topically applied active agents.

In accordance with an important feature of the present invention, a topically applied compound for providing additional cosmetic or therapeutic effects can be any of a wide variety of compounds, either water soluble or oil soluble.

Such a topically applied active compound, therefore, can be one of, or a mixture of, a cosmetic compound, a medicinally active compound, a compound used in cosmetics or personal care, or any other compound that is useful upon topical application to the skin. Such topically active agents include, but are not limited to, skin-care compounds, plant extracts, antioxidants, insect repellants, counterirritants, vitamins, steroids, antibacterial compounds, antifungal compounds, antiinflammatory compounds, topical anesthetics, sunscreens, optical brighteners, and other cosmetic and medicinal topically effective compounds.

For example, a skin conditioner can be the topically applied compound. Skin conditioning agents include, but are not limited to, humectants, such a fructose, glucose, glycerin, propylene glycol, glycereth-26, mannitol, urea, pyrrolidone carboxylic acid, hydrolyzed lecithin, coco-betaine, cysteine hydrochloride, glucamine, PPG-15, sodium gluconate, potassium aspartate, oleyl betaine, thiamine hydrochloride, sodium laureth sulfate, sodium hyaluronate, hydrolyzed proteins, hydrolyzed keratin, amino acids, amine oxides, water-soluble derivatives of vitamins A, E, and D, amino-functional silicones, ethoxylated glycerin, alpha-hydroxy acids and salts thereof, fatty oil derivatives, such as PEG-24 hydrogenated lanolin, and mixtures thereof. Numerous other skin conditioners are listed in the *CTFA Cosmetic Ingredient Handbook*, First Ed., J. Nikotakis, ed., The Cosmetic, Toiletry and Fragrance Association (1988), (hereafter *CTFA Handbook*), pages 79-84, incorporated herein by reference.

The skin conditioner also can be a water-insoluble ester having at least 10 carbon atoms, and preferably 10 to about 32 carbon atoms. Suitable esters include those comprising an aliphatic alcohol having about eight to about twenty carbon atoms and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight-chained or branched. Suitable esters, therefore, include, for example, but are not limited to:

(a) aliphatic monohydric alcohol esters, including, but not limited to:
myristyl propionate,
isopropyl isostearate,
isopropyl myristate,
isopropyl palmitate,
cetyl acetate,
cetyl propionate,
cetyl stearate,
isodecyl neopentanoate,
cetyl octanoate,
isocetyl stearate;

(b) aliphatic di- and tri-esters of polycarboxylic acid, including, but not limited to:
diisopropyl adipate,
diisostearyl fumarate,
dioctyl adipate, and
triisostearyl citrate;

(c) aliphatic polyhydric alcohol esters, including, but not limited to:
propylene glycol dipelargonate;

(d) aliphatic esters of aromatic acids, including, but not limited to:
$C_{12}$-$C_{15}$ alcohol esters of benzoic acid,
octyl salicylate,
sucrose benzoate, and
dioctyl phthalate.

Numerous other esters are listed in the *CTFA Handbook*, at pages 24 through 26, incorporated herein by reference.

In addition, other compounds can be included in a present composition in an amount sufficient to perform their intended function. For example, sunscreen compounds such as benzophenone-3, tannic acid, uric acids, quinine salts, dihydroxy naphtholic acid, an anthranilate, p-aminobenzoic acid, phenylbenzimidazole sulfonic acid, PEG-25, or p-aminobenzoic acid can be used as the topically applied compound. Further, sunscreen compounds such as dioxybenzone, ethyl 4-[bis (hydroxypropyl)] aminobenzoate, glyceryl aminobenzoate, homosalate, methyl anthranilate, octocrylene, octyl methoxycinnamate, octyl salicylate, oxybenzone, padimate O, red petrolatum, titanium dioxide, 4-menthylbenzylidene camphor, benzophenone-1, benzophenone-2, benzophenone-6, benzophenone-12, isopropyl dibenzoyl methane, butyl methoxydibenzoylmethane, zotocrylene, or zinc oxide can be used as the topically applied compound. Other sunscreen compounds are listed in *CTFA Handbook*, pages 86 and 87, incorporated herein by reference.

Similarly, topically applied drugs, like antifungal compounds, antibacterial compounds, antiinflammatory compounds, topical anesthetics, skin rash, skin disease, and dermatitis medications, and antiitch and irritation-reducing compounds can be used as the active agent in the compositions of the present invention. For example, analgesics such as benzocaine, dyclonine hydrochloride, aloe vera, and the like; anesthetics such as butamben picrate, lidocaine hydrochloride, xylocaine, and the like; antibacterials and antiseptics, such as povidone-iodine, polymyxin b sulfate-bacitracin, zinc-neomycin sulfate-hydrocortisone, chloramphenicol, ethylbenzethonium chloride, erythromycin, and the like; antiparasitics, such as lindane; essentially all dermatologicals, like acne preparations, such as benzoyl peroxide, erythromycin benzoyl peroxide, clindamycin phosphate, 5,7-dichloro-8-hydroxyquinoline, and the like; antiinflammatory agents, such as alclometasone dipropionate, betamethasone valerate, and the like; burn relief ointments, such as o-amino-p-toluenesulfonamide monoacetate, and the like; dermatitis relief agents, such as the active steroid amcinonide, diflorasone diacetate, hydrocortisone, and the like; diaper rash relief agents, such as methylbenzethonium chloride, and the like; emollients and moisturizers, such as mineral oil, PEG-4 dilaurate, lanolin oil, petrolatum, mineral wax, and the like; fungicides, such as butocouazole nitrate, haloprogin, clotrimazole, and the like; herpes treatment drugs, such as O-[(2-hydroxymethyl)-methyl]guanine; pruritic medications, such as alclometasone dipropionate, betamethasone valerate, isopropyl myristate MSD, and the like; psoriasis, seborrhea, and scabicide agents, such as anthralin, methoxsalen, coal tar, and the like; steroids, such as 2-(acetyloxy)-9-fluoro-1',2',3',4'-tetrahydro-11-hydroxypregna-1,4-dieno-[16,17-b]naphthalene-3,20-dione and 21-chloro-9-fluoro-1',2',3',4'-tetrahydro-11b-hydroxypregna-1,4-dieno-[16,17-b]naphthalene-3,20-dione. Any other medication capable of topical administration, like skin protectants, such as allantoin, and antiacne agents, such as salicylic acid, also can be incorporated in a composition of the present invention in an amount sufficient to perform its intended function. Other topically applied compounds are listed in *Remington's Pharmaceutical Sciences,* 17th Ed., Mack Publishing Co., Easton, Pa. (1985), pages 773-791 and pages 1054-1058 (hereinafter *Remington's*), incorporated herein by reference.

The topically active compound also can be up/ant extract or a natural oil. Nonlimiting plant extracts are those obtained from alfalfa, aloe vera, amla fruit, angelica root, anise seed, apple, apricot, artichoke leaf, asparagus root, banana, barberry, barley sprout, bee pollen, beet leaf, bilberry fruit, birch leaf, bitter melon, black currant leaf, black pepper, black walnut, blueberry, blackberry, burdock, carrot, cayenne, celery seed, cherry, chickwood, cola nut, corn silk, cranberry, dandelion root, elderberry, eucalyptus leaf, flax oil powder, ginger root, gingko leaf, ginseng, goldenrod, goldenseal, grape, grapefruit, guava, hibiscus, juniper, kiwi, kudzu, lemon, licorice root, lime, matt, marigold, myrrh, olive leaf, orange fruit, orange peel, oregano, papaya fruit, papaya leaf, passion fruit, peach, pear, pine bark, plum, pomegranate, prune, raspberry, rhubarb root, rosemary leaf, sage leaf, spearmint leaf, St. John's wart, strawberry, sweet cloves, tangerine, violet herb, watercress, watermelon, willow bark, wintergreen leaf, witch hazel bark, yohimbe, and yucca root. An example of a natural oil is rice bran oil.

The present compositions can be admixed with other ingredients traditionally included in cosmetic, dermatological, medicinal, and other such compositions. These ingredients include, but are not limited to, dyes, fragrances, preservatives, antioxidants, detackifying agents, and similar types of compounds. The ingredients are included in the composition in an amount sufficient to perform their intended function.

The following additional ingredients typically are included in a present composition. Each of these ingredients, and any other ingredient, is present in a sufficient amount to perform its intended function, without adversely affecting the efficacy of the composition.

In some preferred embodiments, a present composition can contain a thickening or gelling agent. A thickening or gelling agent can be, for example, a polymer that is water soluble or that generates a colloidal solution in water. A thickening or gelling agent, therefore, can be, for example, polymers or copolymers unsaturated carboxylic acids or unsaturated esters, polysaccharide derivatives, gums, colloidal silicates, polyethylene glycols (PEG) and their derivatives, polyvinylpyrrolidones and their derivatives, polyacrylamides and their derivatives, polyacrylonitriles, hydrophilic silica gels, or mixtures thereof.

Specific thickening or gelling agents can be, for example, acrylic and/or methacrylic polymers or copolymers, vinylcarboxylic polymers, polyglyceryl acrylates or methacrylates, polyacrylamides derivatives, cellulose or starch derivatives, chitin derivatives, alginates, hyaluronic acid and its salts, chonodroitin sulphates, xanthan, gellan, Rhamsan, karaya or guar gum, carob flour, and colloidal aluminum magnesium silicates of the montmorillonite type.

Additional thickening or gelling agents include vinylcarboxylic polymers sold under the tradename CARBOPOL® (Goodrich), acrylic acid/ethyl acrylate copolymers, acrylic acid/stearyl methacrylate copolymers, carboxymethylcellulose, hydroxymethylcellulose, hydroxypropylcellulose, microcrystalline cellulose, hydroxypropyl guar, colloidal hectorites, bentonites, and the like.

Other classes of optional ingredients included in a present composition can be, but not limited to preservatives, buffering agents, foam stabilizers, opacifiers, and similar classes of ingredients known to persons skilled in the art. Specific optional ingredients include inorganic phosphates, sulfates, and carbonates as buffering agents; and acids and bases as pH adjusters.

Nonlimiting examples of basic pH adjusters are ammonia; mono-, di-, and tri-alkyl amines; mono-, di-, and tri-alkanolamines; alkali metal and alkaline earth metal hydroxides; and mixtures thereof. Specific, nonlimiting examples of basic pH adjusters are ammonia; sodium, potassium, and lithium hydroxide; monoethanolamine; triethylamine; isopropanolamine; diethanolamine; and triethanolamine. Examples of acidic pH adjusters are the mineral acids and organic carboxylic acids. Nonlimiting examples of mineral acids are citric acid, hydrochloric acid, nitric acid, phosphoric acid, and sulfuric acid.

A composition of the present invention is topically applied to the skin as needed. Typically, the composition is topically applied to the skin one to four times per day. However, application of a present composition can be more or less frequent as prescribed, required, or desired. The present compositions are applied to the skin by spraying or rubbing. The preferred route of administration is rubbing onto the skin with a soft massage to ensure intimate contact with the skin.

Obviously, many modifications and variations of the invention as hereinbefore set forth can be made without departing from the spirit and scope thereof and, therefore, only such limitations should be imposed as are indicated by the appended claims.

What is claimed is:

1. A water-in-oil emulsion containing composition comprising: a. a water-in-oil emulsion, and b. a retinoid loaded onto polymeric microparticles, wherein the microparticles are dispersed in the oil phase, and having a pH below 5.0, wherein the composition retains greater than 70% by weight of the retinoid present in the composition after 24 weeks at 40° C., or greater than 70% by weight of the retinoid present in the composition after 12 weeks at 45° C., and wherein the composition includes about 50% to about 80% by weight water.

2. The composition of claim 1 wherein said retinoid is selected from the group consisting of all-trans retinol, retinol, retinaldehyde, retinal, retinyl acetate, retinyl palmitate, retinoic acid, retinyl propionate, retinyl linoleate, dehydroretinol, eretinate, eretrin, motretinide, a synthetic retinoid, and mixtures thereof.

3. The composition of claim 1 comprising about 0.01% to about 2% retinoid by weight of the composition.

4. The composition of claim 1 wherein the retinoid is loaded onto the polymeric microparticles in an amount to provide loaded microparticles containing about 2% to about 80% of the retinoid, by weight.

5. The composition of claim 4 wherein the polymeric microparticles are selected from the group consisting of a copolymer of allyl methacrylate and ethylene glycol dimethacrylate, a copolymer of ethylene glycol dimethacrylate and lauryl methacrylate, a copolymer of methyl methacrylate and ethylene glycol dimethacrylate, a copolymer of 2-ethylhexyl acrylate, styrene, and divinylbenzene, and mixtures thereof.

6. The composition of claim 1 wherein the polymeric microparticles comprise a copolymer of allyl methacrylate and ethylene glycol dimethacrylate, a copolymer of ethylene glycol dimethacrylate and lauryl methacrylate, or a mixture thereof.

7. The composition of claim 5 wherein the polymeric microparticles comprise a copolymer of ethylene glycol dimethacrylate and methyl methacrylate.

8. The composition of claim 1 further comprising a dermatologically active acid selected from the group consisting of an alpha-hydroxy carboxylic acid, a beta-hydroxy carboxylic acid, ascorbic acid, and mixtures thereof.

9. The composition of claim 8 wherein the alpha-hydroxy acid comprises citric acid, glycolic acid, lactic acid, a salt thereof, or mixtures thereof.

10. The composition of claim 8 wherein the beta-hydroxy acid comprises salicylic acid.

11. The composition of claim 8 comprising about 0.03% to about 10% of the active acid by weight of the composition.

12. The composition of claim 9 comprising about 0.1% to about 10% of the active acid, by weight of the composition, and about 0.01% to about 2% of the retinoid, by weight of the composition.

13. The composition of claim 10 comprising about 0.03% to about 10% salicylic acid, by weight of the composition, and about 0.01% to about 2% of the retinoid, by weight of the composition.

14. The composition of claim 1 further comprising a chelating agent.

15. The composition of claim 14 further comprising an oil-soluble antioxidant.

16. The composition of claim 14 wherein the chelating agent is selected from the group consisting of ethylenediaminetetraacetic acid, diethylenetriaminepentaacetic acid (DTPA), N-(hydroxy ethyl)ethylenediaminetriacetate acid (HEDTA), nitrilotriacetic acid, a salt thereof, a derivative thereof, and mixtures thereof.

17. The composition of claim 15 wherein the oil-soluble antioxidant comprises butylated hydroxytoluene, butylated hydroxyanisole, ascorbyl palmitate, alpha-tocopherol, or mixtures thereof.

18. The composition of claim 14 wherein the chelating agent is present in an amount of about 0.01% to about 1% by weight of the composition.

19. The composition of claim 15 wherein the antioxidant is present in an amount of about 0.01% to about 1%, by weight of the composition.

20. A method of treating mammalian skin comprising contacting the skin with a composition of claim 1 in a sufficient amount to reduce fine lines and wrinkles in the skin.

21. The method of claim 20 wherein the mammalian skin is human skin.

* * * * *